(12) United States Patent
Slatkin et al.

(10) Patent No.: US 9,539,443 B2
(45) Date of Patent: Jan. 10, 2017

(54) SAFETY METHODS AND APPARATUS FOR LOW DOSE-RATE RADIATION FOR MEDICAL AND VETERINARY THERAPIES

(71) Applicant: MICROBEAM THERAPY, LLC, Redwood City, CA (US)

(72) Inventors: Daniel N. Slatkin, Essex, CT (US); Fred Harden Geisler, Chicago, IL (US)

(73) Assignee: MICROBEAM THERAPY, LLC., Redwood City, CA (US)

( * ) Notice: Subject to any disclaimer, the term of this patent is extended or adjusted under 35 U.S.C. 154(b) by 743 days.

(21) Appl. No.: 13/853,372

(22) Filed: Mar. 29, 2013

(65) Prior Publication Data

US 2014/0294153 A1 Oct. 2, 2014

(51) Int. Cl.
*A61N 5/10* (2006.01)

(52) U.S. Cl.
CPC ........... *A61N 5/1064* (2013.01); *A61N 5/1042* (2013.01); *A61N 2005/1095* (2013.01)

(58) Field of Classification Search
CPC ........ G01N 23/04; G01N 30/74; G01N 21/33; G01N 15/082; G01N 2033/0096; G01N 30/7266; G01N 17/004; G01N 2021/335; G01N 21/05; G01N 21/9501; G01N 23/2273; G01N 27/622; G01N 30/02; G01N 33/00; G01N 33/0004; G01N 15/1404; G06T 2207/10116; G06T 2207/30004; G06T 2200/28; G06T 5/002; G06T 2207/20061; G06T 5/009; G06T 5/40; G06T 5/50; G06T 7/0012; G06T 7/0083; H01L 2924/0002; H01L 27/14609; H01L 2924/00; H01L 27/14603; A61N 5/1064; A61N 2005/1095; A61N 5/1042
USPC .................................. 378/62, 92, 65, 98.7
See application file for complete search history.

(56) References Cited

U.S. PATENT DOCUMENTS

| | | | |
|---|---|---|---|
| 5,339,347 A | | 8/1994 | Slatkin et al. |
| 5,619,042 A | * | 4/1997 | Hughes ....................... 250/492.3 |
| 5,625,663 A | * | 4/1997 | Swerdloff ............ A61N 5/1042 378/113 |
| 5,771,270 A | | 6/1998 | Archer |
| 6,714,627 B1 | * | 3/2004 | Brown ................ A61N 5/1042 378/152 |
| 6,921,200 B1 | * | 7/2005 | Booysen et al. ............. 378/205 |
| 7,476,027 B2 | * | 1/2009 | Takenaka et al. ............. 378/207 |
| 2003/0174808 A1 | * | 9/2003 | Hughes ................ A61N 5/1048 378/65 |
| 2006/0176997 A1 | | 8/2006 | Dilmanian et al. |
| 2010/0260317 A1 | * | 10/2010 | Chang et al. .................. 378/62 |

(Continued)

OTHER PUBLICATIONS

International Search Report in corresponding PCT Application No. PCT/US2013/025267, issued on Apr. 3, 2013.

(Continued)

*Primary Examiner* — Glen Kao
(74) *Attorney, Agent, or Firm* — Kramer Amado P.C.

(57) ABSTRACT

Various embodiments relate to a microbeam radiation therapy (microbeam radiosurgery) system, including: a radiation beam source; a collimator with slits, wherein the collimator only passes a radiation beam from the radiation beam source through the slits; a filtering and limiting system; a source shutoff controller connected to the radiation beam source; and a detector configured to detect events requiring the shutdown of the radiation beam source.

7 Claims, 3 Drawing Sheets

(56) References Cited

U.S. PATENT DOCUMENTS

2011/0200170 A1* 8/2011 Nord et al. .................. 378/65
2011/0228907 A1* 9/2011 Gagnon .............. A61N 5/1049
378/65

OTHER PUBLICATIONS

Ahunbay et al, "Direct Aperture Optimization-Based Intensity-Modulated Radiotherapy for Whole Breast Irradiation", Int. J. Radiation Oncology Biol. Phys., vol. 67, No. 4, 2007, pp. 1248-1258.

Slatkin et al, "Prospects for Microbeam Radiation Therapy of Brain Tumours in Children", Medical Department Brookhaven National Laboratory, 2008, p. 163.

W.P.M. Mayles, "Survey of the Availability and Use of Advanced Radiotherapy Technology in the UK", Clinical Oncology 22 (2010) pp. 636-642.

Beilajew, "The Effect of Strong Longitudinal Magnetic Fields on Dose Deposition from Electron and Photon Beams", Med. Phys. 20 (4), Jul./Aug. 1993, pp. 1171-1179.

Keall et al, "Electromagnetic-Guided Dynamic Multileaf Collimator Tracking Enables Motion Management for Intensity-Modulated ARC Therapy", Int. J. Radiation Oncology Biol. Phys., vol. 79, No. 1, 2011, pp. 312-320.

E. Brauer-Krisch et al, "Characterization of a Tungsten/Gas Multislit Collimator for Microbeam Radiation Therapy at the Europeam Synchrotron Radiation Facility", Review of Scientific Instruments 76, 2005, 7 pages.

E. Brauer-Krisch et al, "Effects of Pulsed, Spatially Fractionated, Microscopic Synchrotron X-Ray Beams on Normal and Tumoral Brain Tissue", Mutation Research 704/Reviews in Mutation Research, (2010), pp. 160-166.

E. Brauer-Krisch, "New Technology Enables High Precision Multislit Collimators for Microbeam Radiation Therapy", Review of Scientific Instruments 80, (2009), 6 pages.

Jian-Rong Dai et al, "Intensity-Modulation Radiotherapy Using Independent Collimators: An Algorithm Study", Med. Phys. 26 (12), 1999, pp. 2562-2570.

Hargrave et al, "Diffuse Brainstem Glioma in Children: Critical Review of Clinical Trials", http://oncology.thelancet.com, vol. 7, 2006, pp. 241-248.

Kalef-Ezra, "Health Physics Aspects in Treatment Rooms After 18-MV X-Ray Irradiations", Radiation Protection Dosimetry (2011), vol. 147, No. 1-2, pp. 1-6.

J.A. Laissue et al, "Prospects for Microbeam Radiation Therapy of Brain Tumours in Children to Reduce Neurological Sequelae", Developmental Medicine & Child Neurology, 2007, 49: 577-581.

Laissue et al, "The Weanling Piglet Cerebellum: A Surrogate for Tolerance to MRT (Microbeam Radiation Therapy) in Pediatric Neuro-Oncology", Proceedings of SPIE, vol. 4508 (2001), pp. 65-73.

Fan et al, "Intensity Modulation Under Geometrical Uncertainty: A Deconvolution Approach to Robust Fluence", Physics in Medicine and Biology 55 (2010), pp. 4029-4045.

Bert et al, "Motion in Radiotherapy: Particle Therapy", Physics in Medicine and Biology 56 (2011), pp. R113-R144.

Serduc et al, High-Precision Radiosurgical Dose Delivery by Interlaced Microbeam Arrays of High-Flux Low-Energy Synchrotron X-Rays, Synchrotron X-Ray Radiosurgery, vol. 5, issue 2, 2010, pp. 1-12.

Slatkin, "Uniaxial and Biaxial Irradiation Protocols for Microbeam Radiation Therapy", Institute of Physics Publishing, Phys. Med. Biol. 49 (2004), pp. N203-N204.

Slatkin, "Tetrahedral Irradiation Protocol for Microbeam Radiation Therapy", Institute of Physics Publishing, Phys. Med. Biol. 51 (2006), pp. N295-N297.

Cai et al, "Targeted Cancer Therapy with Tumor Necrosis Factor-Alpha", Biochemistry Insights, 2008, pp. 5-21.

Gonsalves et al, "Tunable Laser Plasma Accelerator Based on Longitudinal Density Tailoring", Nature Physics, 2011, pp. 1-5.

Esteban et al, "Reducing the Number of Segments in Unidirectional Segmentations of Fluence Matrices for Muitileaf Collimators in IMRT", M.Sc. Biomedical Engineering, 2010, pp. i-xii and 1-30.

\* cited by examiner

SAFETY METHODS AND APPARATUS FOR LOW DOSE-RATE RADIATION FOR MEDICAL AND VETERINARY THERAPIES

TECHNICAL FIELD

Various exemplary embodiments disclosed herein relate generally to safety methods and apparatus for low-dose-rate (LDR) radiation for medical and veterinary therapies.

BACKGROUND

Cancer continues to be one of the foremost health problems. Conventional treatments such as surgery and chemotherapy have been extremely successful in certain cases; in other instances, much less so. Radiation therapy has also exhibited favorable results in many cases, while failing to be completely satisfactory and effective in all instances. An alternative form of radiation therapy, known as microbeam radiation therapy (MRT) or microbeam radiosurgery (MBRS) may be used to treat certain tumors for which the conventional methods have been ineffective.

MBRS differs from conventional radiation therapy by employing multiple parallel fan beams of radiation with a narrow dimension or thickness that may be on the order of 10 micrometers to 200 micrometers. The thickness of the microbeams is dependent upon the capacity of tissue surrounding a beam path to support the recovery of the tissue injured by the beam. It has been found that certain types of cells, notably endothelial cells lining blood vessels, but also oligodendroglial and other supporting cells, have the capacity to migrate over microscopic distances, infiltrating tissue damaged by radiation and reducing tissue necrosis in the beam path. In MBRS, sufficient unirradiated or minimally irradiated microscopic zones remain in the normal tissue, through which the microbeams pass, to allow efficient repair of irradiation-damaged tissue. As a result, MBRS is fundamentally different from other forms of radiation therapy.

In conventional forms of radiation therapy, including the radiosurgical techniques employing multiple convergent beams of gamma radiation, each beam is at least five hundred micrometers wide, so that the biological advantage of rapid repair by migrating or proliferating endothelial cells is minimal or nonexistent. Observations of the regeneration of blood vessels following MBRS indicate that endothelial cells cannot efficiently regenerate damaged blood vessels over distances on the order of more than 100 micrometers (μm). Thus, in view of this knowledge concerning radiation pathology of normal blood vessels, the skilled artisan may select a microbeam thickness as small as 20 μm but not more than 100 μm. Further, the microbeams may include substantially parallel, non-overlapping, planar beams with center-to-center spacing of from about 50 μm to about 500 μm. Also, the beam energies may range from about 30 to several hundred keV. These microbeams result in a dosage profile with peaks and valleys. The radiation dosage in the peaks is large enough to kill the targeted tumor, but also kills healthy cells in the peak dosage areas. The region between the peaks is called the valley region. The minimum radiation dosage in the valleys (i.e., the "nadir" valley dosage) is small enough to prevent clonogenically lethal damage to all potentially reparative cells in the valley dosage areas.

A division of a radiation beam into microbeams and the use of a patient exposure plan that provides non-overlapping beams in the tissue surrounding the target tumor allows the non-target tissue to recover from the radiation injury by migration of regenerating endothelial and other reparative cells of the small blood vessels to the areas in which the endothelial cells have been injured beyond recovery. Therefore, the probability of radiation-induced coagulative necrosis in normal, non-targeted tissue is lowered, which may improve the effectiveness of clinical radiation therapy for deep-seated and/or superficially situated tumors.

Various studies have shown the microbeam tissue-sparing effect for X-ray microbeams. Although other methods and processes are known for radiation therapy, none provides a method for performing radiation therapy while avoiding significant radiation-induced damage to tissues proximal to, distal to, and interspersed with the targeted lesion.

Present radiation therapies often take many days and weeks of treatment to provide enough radiation to a target tumor. On the other hand, MBRS can provide an effectual treatment in single visit. Very high-energy radiation may be used with MBRS that results in the destruction of tumor tissue while allowing for the regeneration of healthy tissue affected by the microbeams.

Further, MBRS provides a method for treating cancerous tumors by using extremely narrow, quasi-parallel X-ray microbeams increasing the precision and accuracy of radiation therapy. MBRS also provides a method of using extremely small microbeams of radiation to unexpectedly produce effective radiation therapy while avoiding significant radiation-induced damage to non-targeted tissues.

A major benefit of MBRS is that the microbeams are so narrow that the vasculature of the tissue and other components of the tissue through which the microbeams pass can repair themselves by the infiltration of endothelial cells and other cells from surrounding unirradiated tissue. Present knowledge indicates that such infiltration can take place only over distances on the order of less than 500 μm and depends on the specific tissue being irradiated. The dimensions of the microbeams and the configuration of the microbeam array are therefore determinable with reference to the susceptibility to irradiation of the target tissue and the surrounding tissue to irradiation and the capacities of the various involved tissues to regenerate.

Because the high-energy beam used in MBRS is very powerful, great care must be used during MBRS treatments. Even brief exposure the full high-energy beam may cause great damage and even lead to death. Further, effective MBRS requires very careful targeting of the microbeams, so any movement, even very small movements, can lead not only to ineffective treatment, but significant damage to the subject. Accordingly, safety protocols and systems must be used to provide safe MBRS treatment to the subject. Also, individuals administering the MBRS treatment must be kept safe, so such safety protocols and systems should be designed to protect them as well.

U.S. Pat. No. 5,339,247 to Slatkin et al. titled Method for Microbeam Radiation Therapy provides background related to MBRS, and is hereby incorporated by reference for all purposes as if fully set forth herein.

SUMMARY

Accordingly, there is a need for safety methods and apparatus for MBRS that project the subject being treated and the individuals administering the MBRS.

A brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in the later sections.

Various embodiments may also relate to a microbeam radiation therapy system, including: a radiation beam source; a collimator with slits, wherein the collimator only passes a radiation beam from the radiation beam source through the slits; a filtering and limiting system; a source shutoff controller connected to the radiation beam source; and a detector configured to detect events requiring the shutdown of the radiation beam source.

Various embodiments may also relate to a method of preparing for performing microbeam radiation therapy treatment on a subject, including: calculating a radiation dose; determining that the calculated radiation dose corresponds to the treatment region; performing a trial run of the treatment without the radiation beam; and performing a trial run of the treatment with the radiation beam to verify dose and treatment area.

BRIEF DESCRIPTION OF THE DRAWINGS

In order to better understand various exemplary embodiments, reference is made to the accompanying drawings wherein.

DETAILED DESCRIPTION

Figure 1:
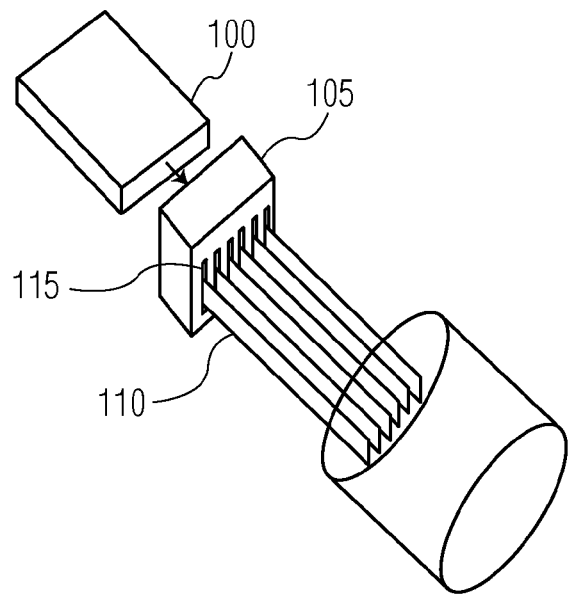
FIG. 1 illustrates a method for producing microbeams using a collimator.

Referring now to the drawings, in which like numerals refer to like components or steps, there are disclosed broad aspects of various exemplary embodiments.

FIG. 1 illustrates a method for producing microbeams using a collimator. The collimator 105 may include a plurality of parallel slits 115 in a vertical direction. A high-energy radiation fan beam 100 that may be very narrow in the vertical direction and wide in the horizontal direction may pass through the collimator 105. Because the collimator 105 is made of a high-Z material, it blocks portions of the of the high-energy radiation fan beam 100. The portion of the high-energy radiation fan beam 100 that passes through the slits 115 of the collimator 105 forms the microbeams 110. The microbeams 110 may be used to treat a subject. Depending upon the vertical height of the fan beam 100 relative to the size of the treatment region, the subject may have to be moved relative to the microbeams 110 in order to irradiate the whole treatment region. It may not be possible to move the high-energy radiation fan beam 100 because of the massive size of the facility necessary to produce the high-energy radiation fan beam 100. Further, the collimator 105 may be fixed relative to the high-energy fan beam 100.

MBRS may apply very high-energy radiation beams for a very short period of time. One problem with MBRS may occur when the subject moves relative to the beam during treatment. This may result in smearing of the peak and valley doses applied to the subject. Effective and safe MBRS relies upon valley dose regions where the radiation dose is low enough to prevent any damage to the healthy cells in the valley dose regions. If the subject moves relative to the microbeams 110 during treatment, then the high-energy radiation of the microbeams 110 may smear into the valley dose regions resulting in many if not all of the healthy cells along the path of the microbeams 110 being injured beyond recovery. Accordingly there is a need to prevent smearing of the peak and valley doses.

The microbeams 110 may be fixed relative to the subject by affixing a collimator to the subject that splits a high-energy fan beam 100 into microbeams 110. In this embodiment, even though the subject may move relative to the high-energy fan beam 100, the collimator moves with the subject, hence the microbeams 115 emanating from the collimator move with the subject as well. Alternatively, the collimator may be fixed independently of the subject, and in such situations the movement of the subject should be minimized.

Figure 2:
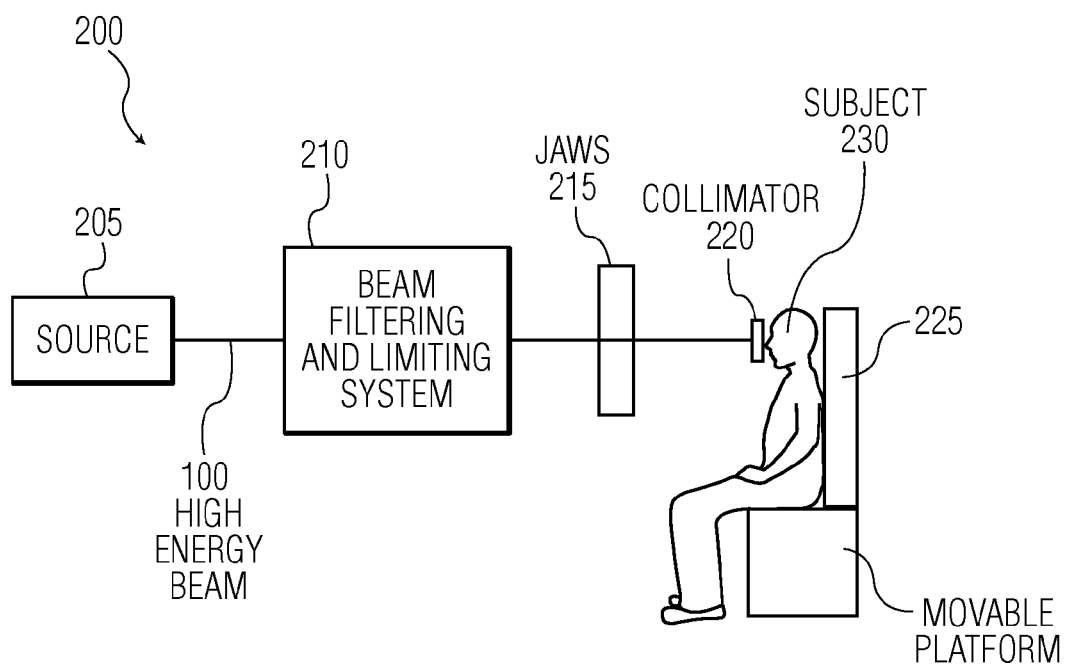
FIG. 2 illustrates an embodiment of a MBRS system.

FIG. 2 illustrates an embodiment of a MBRS system. The MBRS system 200 may include a source 205 that produces a high-energy fan beam 100, a beam filtering and limiting system 210, jaws 215, a collimator 220, and a movable platform 225. A subject 230 may be treated by the MBRS system 200.

The source 200 may produce high-energy electromagnetic radiation beam such as X-ray or gamma radiation beam. High-energy X-ray radiation may be especially beneficial. In any generated photon beam, the photons are produced having a characteristic spectrum of energies. The photon energy of the beams range optimally from about 30 keV to about 300 keV, but other energies, in particular lower energies, may also prove useful for MBRS under special circumstances.

A synchrotron may be used to generate an X-ray beam having practically no divergence and a very high fluence-rate (i.e., a high flux of radiant energy). These synchrotron generated X-rays have the potential for projecting sharply defined beam edges deep in the body. This source may be useful for generating X-ray microbeams for radiobiology, radiotherapy, and radiosurgery. A high fluence-rate is required to implement MBRS because exposure times must be short enough (e.g., less than about 1 second) to avoid the blurring of margins of the irradiated zones of tissue due to body or organ movements. Sharply defined microbeam margins are made possible not only by the high fluence-rate and the minimal divergence of the synchrotron beam. Absorbed doses to non-targeted tissues situated between microbeams may be kept below the threshold for radiation damage in tissues both proximal and distal to the isocentric target, i.e., where the microbeams do not overlap. These factors make it possible to effectively irradiate a target using a field of many well defined, closely spaced microbeams.

The radiation beam for producing the microbeam array may be obtained from industrial X-ray generators or from synchrotron beamlines at electron storage rings. The radiation beam may be obtained from a wiggler beam line or from an undulator beam line at an electron storage ring. A conventional "planar" wiggler uses periodic transverse magnetic fields to produce a beam with a rectangular cross-section, typically having a horizontal to vertical beam opening angle ratio on the order of 50:1. In an alternative embodiment, the radiation beam is obtained from a "helical" wiggler, a configuration capable of producing a substantially less anisotropic beam. While a fan beam is discussed in the embodiment below, it is also possible to place the subject to be treated a large distance (i.e., >100 m) from the source 200, which may allow the X-ray beam from the source to expand enough in both the horizontal and vertical directions so that the beam covers the whole treatment region, and hence, it may not be necessary to move the subject relative to the high-energy beam, which would be a major advantage over the clinical MBRS systems constructed or publicly disclosed in the archival medical or patent literature to date. Further, such beam spreading could be accomplished by two orthogonal wigglers that would spread the beam first in one direction and concomitantly or sequentially in a second orthogonal direction. Such embodiments would not require movement of the subject as a whole through the microbeam array as is required in the presently publicized art of MBRS, but the collimator may still be affixed to the subject advantageously as described in our previously disclosed embodiments.

The beam filtering and limiting system 210 (which may also be called a beam shaper) filters and limits the high-energy beam 100 for treating the subject 230. As mentioned above the source may produce a high-energy beam with a range of energies. Often only a certain range of energies may be used to treat the subject. Accordingly, various filters made of various materials may be placed in the path of the high-energy beam to filter out the undesired and/or less desirable energy bands in the high-energy beam. Further, spatial limiting may be used to limit the beam to the desired beam size and geometry. This may help to prevent unwanted and unsafe stray radiation from the source 200. Such spatial limiting may be accomplished, for example, with plates having slits. The plates may be of sufficient thickness and high Z material to block portions of the high-energy beam from the source 200.

Jaws 215 further spatially limit the high-energy beam 100 that has passed though the filtering and limiting system 210. The jaws 215 include one pair of opposing movable jaws (with one wiggler) or two orthogonal pairs of opposing movable jaws (with an orthogonal pair of wigglers) that may be made of a material that completely blocks the high-energy beam 100. Because the width of the high-energy fan beam typically may be wider than the target region, it may be necessary to limit the width of the fan beam to the width of the target region. Thus, as the subject 230 moves relative to the high-energy fan beam 100, the width of the target region varies. Accordingly, the jaws 215 move to adjust the width of the high-energy fan beam 100 to correspond to the width of the target region being irradiated by the high-energy fan beam 100. Prior to the subject being treated using MBRS, the target region is very accurately measured, so that during treatment with the high-energy fan beam 100, the width of the beam can be adjusted to correspond a) to the precise desired treatment region and b) to the precise angle of approach of the microbeams used for any particular angle of approach of the miocrobeams toward the predetermined treatment zone in any particular "treatment fraction" used for the BMRS. This would prevent or minimize useless or harmful irradiation of normal healthy tissues adjacent to the desired, targeted treatment region.

With modern diagnostic technology, the boundaries and composition of tumors and other tissues to be treated using MBRS may be very accurately measured. Such accurate measurements of the treatment region may be used to accurately target the MBRS treatment on the subject. Various methods may be used in order to accomplish this and to do it safely so as to prevent injuring the subject.

Figure 3:
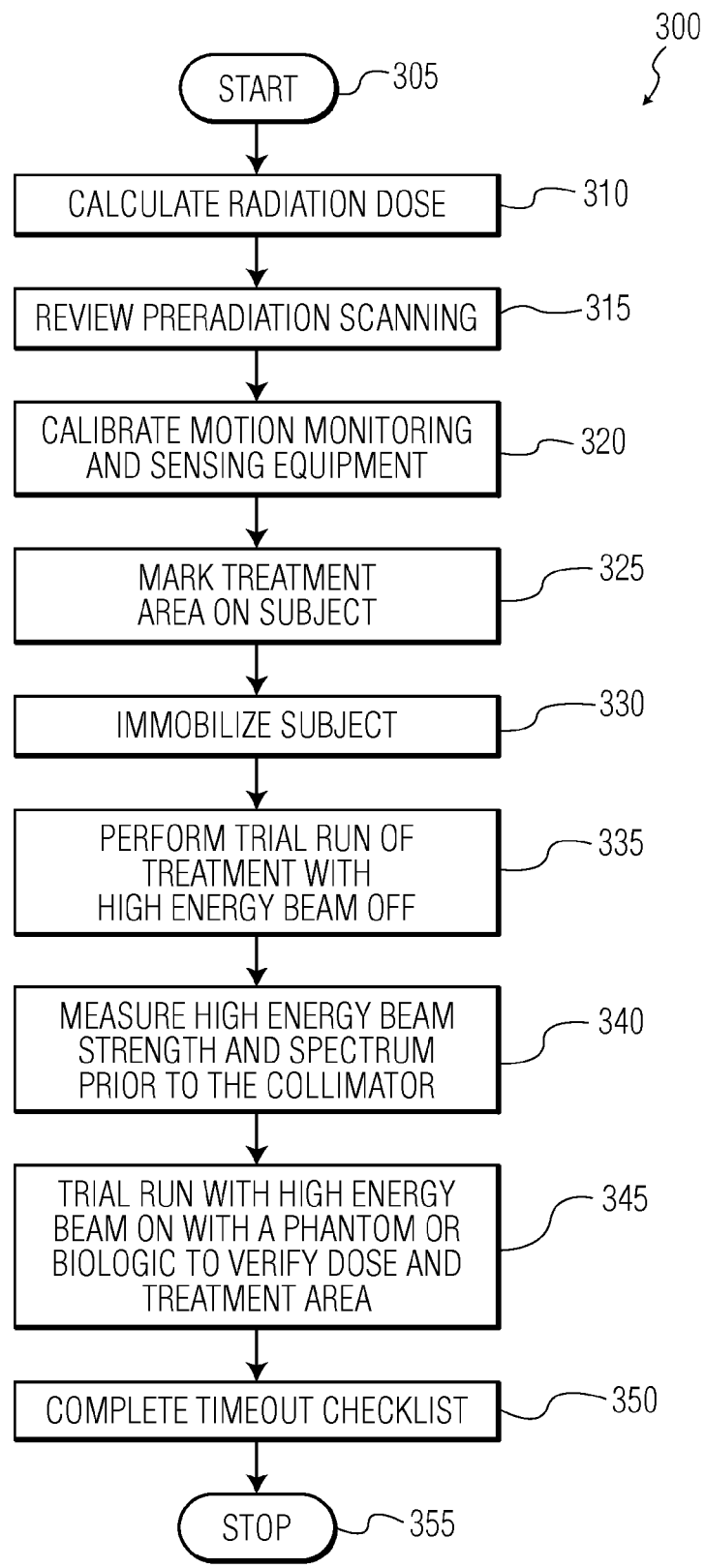
FIG. 3 illustrates a safety method related to a MBRS subject.

FIG. 3 illustrates a safety method related to a MBRS subject. The method 300 begins at step 305. First, the radiation dose may be calculated at step 310. Such calculation may be based upon accurate three-dimensional measurement of the treatment region, e.g., a tumor, using various high-resolution diagnostic and imaging tools. These measurements may include information relating to the composition of the treatment regions. Also, measurements of the tissue between the skin and treatment region should be made, as such tissue will affect the radiation dosage desired. These measurements may then be used to determine the radiation dosage. Various computational tools may be used to determine the dosage.

Next, the pre-radiation scanning may be reviewed at step 315. This review may include determining that any scanning and filtering used to perform the treatment are complete and result in the correct radiation boundaries corresponding to the treatment region.

At step 320, any motion monitoring and sensing equipment must be calibrated and at least pre-tested, optimally post-tested also, to redundantly document the safety of the prior MBRS treatment and further promote the safety of the following MBRS treatment—in other words, implementing every measure humanly possible and technically feasible at the time to assure the safety of MBRS, bearing in mind the reality that no therapeutic medication, surgical maneuver, or any other technique in cancer therapy is or has ever been entirely and assuredly infallible and/or effective and/or palliative in practical clinical use for every patient so treated, while not amenable to any subsequent improvement, MBRS not exceptional, no matter what painstaking measures are undertaken to assure its optimal safety and efficacy. Because precise control of MBRS is required, motion sensing and monitoring equipment may be used to determine that the proper motion is carried out during MBRS and also to determine if any extraneous movement, for example of the subject, is present in order to prevent injury to the subject. Such motion sensing and monitoring equipment may be placed on the subject, the collimator, the beam filtering and limiting system, or any other part of the MBRS system whose movement may affect the safety of the treatment of the subject. The motion and sensing equipment may detect even small movements on the order of micrometers in order to ensure safe treatment of the subject. Also, for elements of the MBRS system that move along a prescribed path during the MBRS treatment, the motion and sensing equipment may detect small variations in the movement of various elements of the MBRS system. Further, such undesired or potentially undesirable motion should also be quickly and automatically detected in order to prevent or minimize injury to the subject by quickly and automatically shut down the exposure. Accordingly, precise and fast motion sensors may be used. Further, this equipment may be calibrated prior to and after treatment in order to ensure in every feasible manner the proper operation of the equipment during and following any particular treatment.

At step 325, the treatment area of the subject may be marked. Such marking may include marking the skin of the subject with a pen to ensure that the proper area is treated. This marked area may be compared to the measurements made of the treatment area. Further, as the subject may be treated multiple times from different directions, multiple markings on the skin may be made in order to ensure each treatment is properly applied.

Next, the subject may be immobilized at step 330. Even small movements of the subject during treatment may result in injury or damage to healthy tissue. Accordingly, immobilizing the patient reduces such injury or damage to the subject. Such immobilization may include subject cooperation, sedation, or anesthesia. Also, sturdy restraints and/or inflatable bags may be used to immobilize the subject while advantageously applying the desired "blanching" of the irradiated skin.

Next, a trial run of the treatment with the high-energy beam turned off may be performed at step 335. This may include a trial run of moving all the equipment in the same manner as would be used during the actual MBRS, but with the radiation source off. This may identify any mechanical obstacles that would prevent the proper and smooth movement of the subject and any other equipment. Further, laser light (or any other light) may be used to trace the path of the high-energy radiation in order to visualize the treatment and to ensure that the proper area of the subject will be treated. Also, an optical detector may be placed in the treatment target area to verify the proposed treatment.

At step 340, the high-energy beam strength may be measured prior to reaching the collimator. A radiation detector may be placed in the path of the high-energy beam prior to reaching the collimator, the high-energy beam may be turned on, and the power of the high-energy beam measured. This measurement may be used to verify that the power of the high-energy beam is neither too high nor too low and that it corresponds to and will enable the desired treatment.

Next, a trial run of the treatment with the high-energy beam on may be made using an inert phantom and/or some living biological preparation to verify the radiation dose and the treatment area. Such a trial run serves as another check that the planned treatment is supplying the proper level of radiation to the correct target area.

At step 350, a timeout checklist may be completed. The timeout checklist may include various steps such as: medical clearance for the procedure; verifying the radiation therapy plan; verifying the identity of the subject; verifying the correct body part to be treated; administering any needed medication prior to treatment; verifying marks on the patient indicating the treatment area; etc. The method 300 may then end at step 355.

The steps in the method 300 may be performed in various other orders. For example, any of steps 335, 340, and 345 may be performed before the subject is immobilized 330. Also, step 325, marking the treatment area on the subject, may be done before or after many of the other steps.

Figure 4:
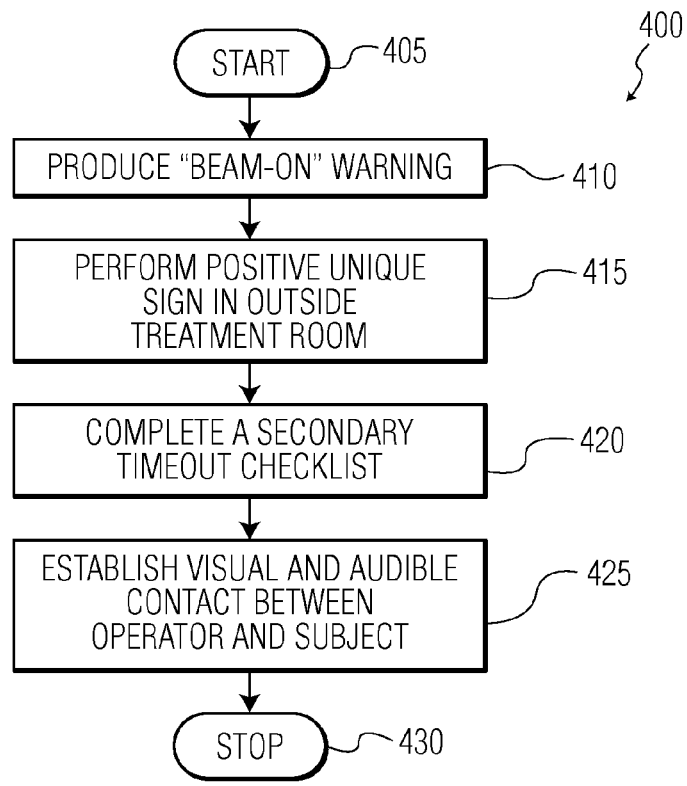
FIG. 4 illustrates a safety method related to individuals administering MBRS.

FIG. 4 illustrates a safety method related to individuals administering MBRS treatment. Safety precautions need to be in place in order to protect various individuals administering the MBRS treatment. Inadvertent irradiation of such an individual may cause injury or even death. The safety method 400 may begin at step 405. At step 410, prior to treatment a beam-on warning may be issued. Such warning may include both audible and visual warnings. Any sort of audible and unique warning may be broadcast coupled with flashing lights or signs indicating that the high-energy beam is about to be switched on.

At step 415, a positive unique sign in outside the treatment room may be performed. Such sign in may require some sort of biometric verification (e.g., thumbprint, voice print, iris scan, etc.), other electronic verification (swipe of ID card, scan for the proximity of an RFID chip, etc.), or even a physical signature. The list of those verified may be compared to those assigned to the treatment team. Also, the identity of all those entering the treatment suite may be logged, and compared to those signed in. Any discrepancies would prevent the treatment from commencing. Also, some sort of detectors may be placed in the treatment area to detect individuals in the treatment area other than the subject to be treated. Such may include motion detectors, IR detectors, video cameras, etc.

Next, a secondary timeout checklist may be completed at step 420. Such a checklist may be the same or similar to the timeout checklist 350. This is another opportunity to verify that various aspects of the treatment are in order.

At step 425, an operator may establish visual and/or audible contact with the subject. This contact may be used to check that the treatment is ready to begin and that the subject is ready. Also, at anytime if the operator identifies a problem before or during the treatment, the operator may shut down the treatment. The method 400 may then end at step 430.

Figure 5:
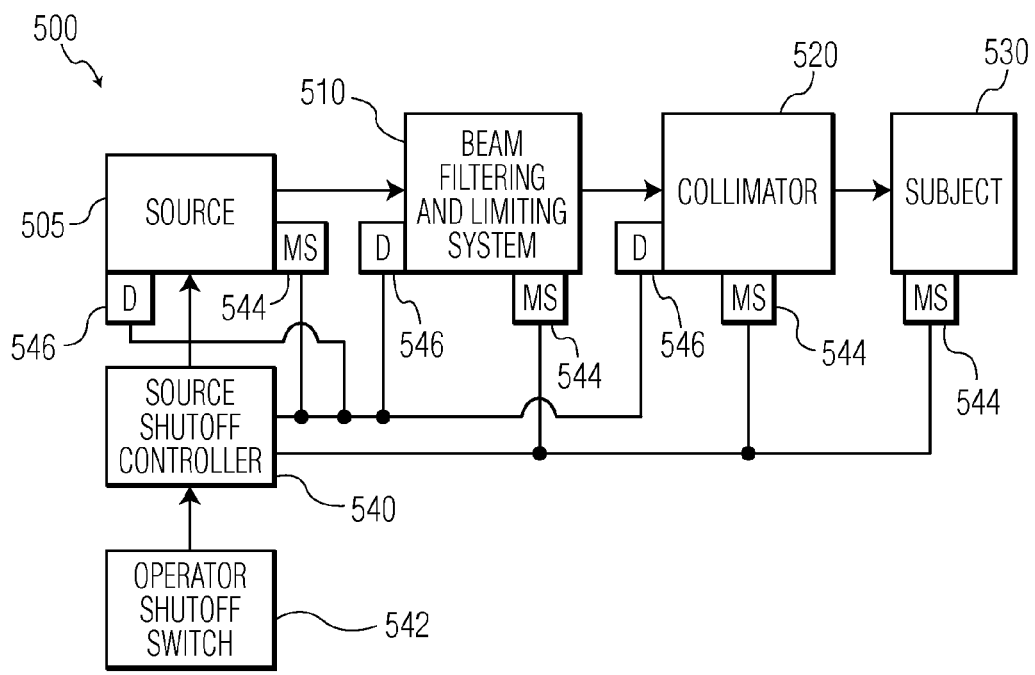
FIG. 5 illustrates a MBRS system with various safety systems.

In addition to various safety procedures used during the treatment, various safety features may be a part of the MBRS system. FIG. 5 illustrates a MBRS system with various safety systems. The MBRS system 500 includes elements like those found in the MBRS system 200 found in FIG. 2. The MBRS system 500 may include a source 505, a beam filtering and limiting system 510, a collimator 520, and a subject 530. These may be like those described above with respect to FIG. 2. The beam filtering and limiting system 510 may also include jaws like those described separately in FIG. 2. The MBRS system 500 further may include a source shutoff controller 540, an operator shutoff switch, radiation detectors 546, and motion sensors 544.

The source shut off controller 540 may control the radiation source 505 and may allow for very fast shut off of the source. The source may be shut off, for example, by a shutter that blocks the output of the source 505. Other shut off methods may be used as well. An operator shutoff switch 542 may be attached to the source shutoff controller 540. The operator switch may be actuated in order to very quickly shut off the radiation source 505. For example, if the operator detects a problem during treatment, the operator may use the operator shutoff switch 542 to very quickly shutoff the radiation source 505.

Further, the source shutoff controller may receive inputs from motion sensors 544 and radiation detectors 546. The motion sensors may be placed on various elements of the MBRS system 500 in order to detect undesired motion that may cause injury to the subject or smearing of the treatment profile. Such movement may include any movement of elements that should be stationary as well as variations in movement from a prescribed path for those elements that move during the treatment. For example, motion sensors 544 may be placed on the radiation source 505, beam filtering and limiting system 544, the collimator 544, and/or the subject 530. The motion sensors 546 may be simple sensors that send motion measurement signals or data to the source shutoff controller 540. In this situation the source shutoff controller 540 may process the various inputs and determine when motion occurs that requires shutting off the radiation source 505. Alternatively, the motion sensors 544 may have processing to determine when motion occurs that requires shutting off the radiation source 505, and the motion sensors 544 would then only send a shut off signal to the source shutoff controller 540. The motion sensors 544 may be able to detect motion as small as, for example, 0.5 to 10 μm. Further, the motion sensors 544 need to quickly identify any motion and send a signal to the source shutoff controller 540 in order to minimize injury to the subject. The motion sensors 544 may be one of any known type of motion sensors.

The radiation detectors 546 may be located anywhere in the MBRS system along the high radiation beam path in order to detect the power of the beam. For example, detectors may be placed at or near the radiation source 505, the beam filtering and limiting system 510, and the collimator 520. The radiation detectors 546 may be simple detectors that send radiation measurement signals or data to the source shutoff controller 540. In this situation the source shutoff controller 540 may process the various inputs and determine when the power of the radiation exceeds a threshold value that requires shutting off the radiation source 505. Alternatively, the radiation detectors 546 may have processing to determine when the power of the radiation exceeds a threshold value that requires shutting off the radiation source 505, and the radiation detectors 546 would then only send a shut off signal to the source shutoff controller 540. The sensors need to quickly identify any increase in beam radiation power above the threshold value and send a signal to the source shutoff controller 540 in order to minimize injury to the subject. The radiation detectors 546 may be one of any known type of radiation detectors.

Further, backup motion sensors 544 and radiation detectors 546 may be present in order to provide redundancy in protecting the subject from injury.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

We claim:

1. A microbeam radiation therapy system, comprising:
   a high-energy electro-magnetic X-ray or gamma ray radiation beam source;
   a collimator with slits, wherein the collimator only passes a radiation beam from the radiation beam source through the slits;
   a beam filtering and limiting system;
   a source shutoff controller connected to the radiation beam source; and
   a detector configured to detect events requiring shutdown of the radiation beam source;
   wherein the detector is a plurality of motion sensors configured to detect motion of the beam filtering and limiting system, collimator, and a subject treated by the microbeam radiation therapy system.

2. The system of claim 1, wherein the detector further comprises a radiation detector configured to detect power of the radiation beam.

3. The system of claim 2, wherein the radiation detector is configured to detect the power of the radiation beam at one of the radiation beam source, beam filtering and limiting system, and collimator.

4. The system of claim 1, wherein the detector further comprises a plurality of radiation detectors configured to detect power of the radiation beam at the beam filtering and limiting system and the collimator.

5. The system of claim 1, wherein the detector further comprises a motion sensor configured to detect motion of the radiation beam source.

6. The system of claim 1, further comprising an operator shutoff switch connected to the source shutoff controller.

7. The system of claim 1, wherein the detector is a plurality of detectors configured to be redundant.

* * * * *